United States Patent
Dietzschold et al.

(10) Patent No.: US 7,695,724 B2
(45) Date of Patent: Apr. 13, 2010

(54) RECOMBINANT RABIES VIRUS COMPOSITIONS

(75) Inventors: Bernhard Dietzschold, Newton Square, PA (US); Marie Luise Faber, Lansdowne, PA (US); Matthias Schnell, Harleysville, PA (US); Milosz Faber, Philadelphia, PA (US)

(73) Assignee: Thomas Jefferson University, Philadelphia, PA (US)

( * ) Notice: Subject to any disclaimer, the term of this patent is extended or adjusted under 35 U.S.C. 154(b) by 0 days.

(21) Appl. No.: 11/571,842

(22) PCT Filed: Jul. 12, 2005

(86) PCT No.: PCT/US2005/024671

§ 371 (c)(1),
(2), (4) Date: Jan. 9, 2007

(87) PCT Pub. No.: WO2006/017276

PCT Pub. Date: Feb. 16, 2006

(65) Prior Publication Data

US 2008/0003657 A1    Jan. 3, 2008

Related U.S. Application Data

(60) Provisional application No. 60/587,129, filed on Jul. 12, 2004.

(51) Int. Cl.
*A61K 39/205* (2006.01)
*C12N 7/00* (2006.01)
*C12N 7/01* (2006.01)
*C12N 15/86* (2006.01)

(52) U.S. Cl. .............. 424/224.1; 435/235.1; 435/320.1; 424/199.1; 424/204.1; 530/350

(58) Field of Classification Search ........................ None
See application file for complete search history.

(56) References Cited

U.S. PATENT DOCUMENTS

| 5,853,735 | A | 12/1998 | Benejean et al. | 424/208.1 |
| 7,074,413 | B2 | 7/2006 | Dietzschold et al. | 424/199.1 |
| 2002/0164356 | A1 | 11/2002 | Mebatsion | 424/205.1 |

FOREIGN PATENT DOCUMENTS

| WO | PCT/US01/09529 | 3/2001 | 39/205 |
| WO | PCT/US02/32475 | 10/2002 | 39/205 |

OTHER PUBLICATIONS

McGettigan et al., Journal of Virology vol. 77, No. 1, pp. 237-244, 2003.*
Ito et al. Microbio and Immunity 1994 vol. 38, pp. 479-482.*
Dietzschold, et al. "In vitro growth and stability of recombinant rabies viruses designed for vaccination of wildlife", *Vaccine* 23 (2004) 518-524.
Faber, et al. "Overexpression of the Rabies Virus Glycoprotein Results in Enhancement of Apoptosis and Antiviral Immune Response", *Journal of Virology*, Apr. 2002, p. 3374-3381.
U.S. Appl. No. 09/816,531, filed Mar. 23, 2001, Dietzschold et al.
U.S. Appl. No. 10/268,197, filed Oct. 10, 2002, Dietzschold et al.
Dietzschold, et al., "Characterization of an Antigenic Determinant of the Glycoprotein that Correlates with Pathogenicty of Rabies Virus," *Proc. Natl. Acad. Sci. USA* 80 pp. 70-74, 1983.
Faber, et al., "A Single Amino Acid Change in Rabies Virus Glycoprotein Increases Virus Spread and Enhances Virus pathogenicity," *Journal of Virology*, 79(22) pp. 14141-14148, 2005.
Mebatsion, et al., "Extensive Attenuation of Rabies Virus by Simultaneously Modifying the Dynein Light Chain Binding Site in the P protein and Replacing Arg333 in the G Protein," *Journal of Virology*, 75(23) pp. 11496-11502, 2001.
Morimoto, et al., "Genetic Engineering of Live Rabies Vaccines," *Vaccine* 19 pp. 3543-3551, 2001.
Seif, et al., "Rabies Virulence: Effect on Pathogenicity and Sequence Characterization of Rabies Virus Mutations Affecting Antigenic Site III of the Glycoprotein," *Journal of Virology* 53(3) pp. 926-934, 1985.

* cited by examiner

*Primary Examiner*—Mary E Mosher
*Assistant Examiner*—Myron G Hill
(74) *Attorney, Agent, or Firm*—Brinker Biddle & Reath LLP; Daniel A. Monaco

(57) ABSTRACT

Recombinant rabies viruses in which the arginine residue of the glycoprotein (G) at amino acid position 333 is exchanged, renders these viruses nonpathogenic for immunocompetent mammals regardless of the route of infection. Some of these recombinant rabies viruses after several serial virus passages in newborn mice can become pathogenic for adult mice. The reversion to the pathogenic phenotype is associated with a thymidine to adenosine mutation (T→A) at position 639 of the G gene, which results in an asparagine to lysine exchange at position 194 of G. The codon at position 637-639 was changed by site directed mutagenesis to replace asparagine at position 194 by an amino acid that minimized the possibility for an Asn→Lys exchange at amino acid position 194 of G and prevents reversion to a pathogenic form of the virus.

10 Claims, 7 Drawing Sheets

Asn$_{194}$ [N] → Lys$_{194}$ [K]

AAT      AAG

Asn$_{194}$ [N] → Ser$_{194}$ [S]

AAT      TCC

Fig. 4 pSPBNGA         3'— I — N — P — M — GA —[BsiW I  Nhe I]— L —5'
                                          └─[Gene Insert]

pSPBNGA-S       3'— I — N — P — M — GAS — L —5' pSPBNGA-S-GA-S  3'— I — N — P — M — GAS — GAS — L —5' pSPBNGA-K       3'— I — N — P — M — GAK — L —5' pSPBNGA-K-GA-K  3'— I — N — P — M — GAK — GAK — L —5'

SEQUENCE LISTING

```
<160> NUMBER OF SEQ ID NOS: 25

<210> SEQ ID NO 1
<211> LENGTH: 27
<212> TYPE: DNA
<213> ORGANISM: Artificial
<220> FEATURE:
<223> OTHER INFORMATION: Primer designated as SADB19 - 120seq(+)

<400> SEQUENCE: 1
aacatgttat ggtgccatta aaccgct                                        27

<210> SEQ ID NO 2
<211> LENGTH: 27
<212> TYPE: DNA
<213> ORGANISM: Artificial
<220> FEATURE:
<223> OTHER INFORMATION: Primer designated as SADB19 +50seq(-)

<400> SEQUENCE: 2
```

```
gggtgttagt ttttttcatg gacttgg                                           27

<210> SEQ ID NO 3
<211> LENGTH: 24
<212> TYPE: DNA
<213> ORGANISM: Artificial
<220> FEATURE:
<223> OTHER INFORMATION: Primer designated as SBsi2seq(+)

<400> SEQUENCE: 3
taattaacgt cctttcaacg atcc                                              24

<210> SEQ ID NO 4
<211> LENGTH: 28
<212> TYPE: DNA
<213> ORGANISM: Artificial
<220> FEATURE:
<223> OTHER INFORMATION: Primer designated as SNhe2seq(-)

<400> SEQUENCE: 4
gagcatcttg aagtaagtag tctcaggt                                          28

<210> SEQ ID NO 5
<211> LENGTH: 1575
<212> TYPE: DNA
<213> ORGANISM: Artificial
<220> FEATURE:
<223> OTHER INFORMATION: Artificial rabies virus glycoprotein with a
      mutation incorporated into the NA sequence to encode a serine at
      position 194

<400> SEQUENCE: 5
atggttcctc aggctctcct gtttgtaccc cttctggttt ttccattgtg ttttgggaaa       60
ttccctattt acacgatacc agacaagctt ggtccctgga gtccgattga catacatcac      120
ctcagctgcc caaacaattt ggtagtggag gacgaaggat gcaccaacct gtcagggttc      180
tcctacatgg aacttaaagt tggatacatc ttagccataa agtgaacgg gttcacttgc      240 acaggcgttg tgacggaggc tgaaacctac actaacttcg ttggttatgt cacaaccacg      300
ttcaaaagaa agcatttccg cccaacacca gatgcatgta gagccgcgta caactggaag      360
atggccggtg accccagata tgaagagtct ctacacaatc gtaccctga ctaccgctgg      420 cttcgaactg taaaaaccac caaggagtct ctcgttatca tatctccaag tgtggcagat      480
ttggacccat atgacagatc ccttcactcg agggtcttcc ctagcgggaa gtgctcagga      540
gtagcggtgt cttctaccta ctgctccact aaccacgatt acaccatttg gatgcccgag      600
aatccgagac tagggatgtc ttgtgacatt tttacctcca gtagagggaa gagagcatcc      660 aagggagtg agacttgcgg cttttgtagat gaaagaggcc tatataagtc tttaaaagga      720
gcatgcaaac tcaagttatg tggagttcta ggacttagac ttatggatgg aacatgggtc      780
tcgatgcaaa catcaaatga aaccaaatgg tgccctcccg ataagttggt gaacctgcac      840
gactttcgct cagacgaaat tgagcacctt gttgtagagg agttggtcag gaagagagag      900
gagtgtctgg atgcactaga gtccatcatg acaaccaagt cagtgagttt cagacgtctc      960
agtcatttaa gaaacttgtg ccctgggttt ggaaaagcat ataccatatt caacaagacc     1020
ttgatggaag ccgatgctca ctacaagtca gtcgagactt ggaatgagat cctcccttca     1080
aaagggtgtt taagttgg ggggaggtgt catcctcatg tgaacggggt gttttttcaat     1140 ggtataatat taggacctga cggcaatgtc ttaatcccag agatgcaatc atccctcctc     1200
```

```
cagcaacata tggagttgtt ggaatcctcg gttatccccc ttgtgcaccc cctggcagac    1260
ccgtctaccg ttttcaagga cggtgacgag gctgaggatt tgttgaagt tcaccttccc     1320 gatgtgcaca atcaggtctc aggagttgac ttgggtctcc cgaactgggg aagtatgta     1380 ttactgagtg caggggccct gactgccttg atgttgataa ttttcctgat gacatgttgt    1440
agaagagtca atcgatcaga acctacgcaa cacaatctca gagggacagg gagggaggtg    1500
tcagtcactc cccaaagcgg gaagatcata tcttcatggg aatcacacaa gagtgggggt    1560
gagaccagac tgtaa                                                     1575
```

<210> SEQ ID NO 6
<211> LENGTH: 9
<212> TYPE: DNA
<213> ORGANISM: Artificial
<220> FEATURE:
<223> OTHER INFORMATION: Artificial rabies virus glycoprotein gene
      sequence of #634-642 in SPBNGA from passage 0

<400> SEQUENCE: 6 accaatagt                                                              9

<210> SEQ ID NO 7
<211> LENGTH: 9
<212> TYPE: DNA
<213> ORGANISM: Artificial
<220> FEATURE:
<223> OTHER INFORMATION: Artificial rabies virus glycoprotein gene
      sequence of #634-642 in SPBNGA from passage 5

<400> SEQUENCE: 7 accaagagt                                                              9

<210> SEQ ID NO 8
<211> LENGTH: 9
<212> TYPE: DNA
<213> ORGANISM: Artificial
<220> FEATURE:
<223> OTHER INFORMATION: Artificial rabies virus glycoprotein gene
      sequence of #634-642 in SPBNGA from passage 10

<400> SEQUENCE: 8 accaagagt                                                              9

<210> SEQ ID NO 9
<211> LENGTH: 9
<212> TYPE: DNA
<213> ORGANISM: Artificial
<220> FEATURE:
<223> OTHER INFORMATION: Artificial rabies virus glycoprotein gene
      sequence of #634-642 of the glycoprotein gene in SPBNGA-cyto c(+)
      from passage 0

<400> SEQUENCE: 9 accaatagt                                                              9

<210> SEQ ID NO 10
<211> LENGTH: 9
<212> TYPE: DNA
<213> ORGANISM: Artificial
<220> FEATURE:
<223> OTHER INFORMATION: Artificial rabies virus glycoprotein gene
      sequence of #634-642 of the glycoprotein gene in SPBNGA-cyto c(+)
      from passage 5

<400> SEQUENCE: 10

-continued

```
<210> SEQ ID NO 11
<211> LENGTH: 9
<212> TYPE: DNA
<213> ORGANISM: Artificial
<220> FEATURE:
<223> OTHER INFORMATION: Artificial rabies virus glycoprotein gene
      sequence of #634-642 of the glycoprotein gene in SPBNGA-cyto c(+)
      from passage 10

<400> SEQUENCE: 11 accaagagt                                                            9

<210> SEQ ID NO 12
<211> LENGTH: 9
<212> TYPE: DNA
<213> ORGANISM: Artificial
<220> FEATURE:
<223> OTHER INFORMATION: Artificial rabies virus first glycoprotein gene
      sequence of #634-642 of the glycoprotein gene in SPBNGA-GA from
      passage 0

<400> SEQUENCE: 12 accaatagt                                                            9

<210> SEQ ID NO 13
<211> LENGTH: 9
<212> TYPE: DNA
<213> ORGANISM: Artificial
<220> FEATURE:
<223> OTHER INFORMATION: Artificial rabies virus first glycoprotein gene
      sequence of #634-642 of the glycoprotein gene in SPBNGA-GA from
      passage 5

<400> SEQUENCE: 13 accaaaagt                                                            9

<210> SEQ ID NO 14
<211> LENGTH: 9
<212> TYPE: DNA
<213> ORGANISM: Artificial
<220> FEATURE:
<223> OTHER INFORMATION: Artificial rabies virus first glycoprotein gene
      sequence of #634-642 of the glycoprotein gene in SPBNGA-GA from
      passage 10

<400> SEQUENCE: 14 accaaaagt                                                            9

<210> SEQ ID NO 15
<211> LENGTH: 9
<212> TYPE: DNA
<213> ORGANISM: Artificial
<220> FEATURE:
<223> OTHER INFORMATION: Artificial rabies virus second glycoprotein
      gene sequence of #634-642 of the glycoprotein gene in SPBNGA-GA
      from passage 0

<400> SEQUENCE: 15 accaatagt                                                            9

<210> SEQ ID NO 16
<211> LENGTH: 9
<212> TYPE: DNA
<213> ORGANISM: Artificial
<220> FEATURE:
<223> OTHER INFORMATION: Artificial rabies virus second glycoprotein
```

```
      gene sequence of #634-642 of the glycoprotein gene in SPBNGA-GA
      from passage 5

<400> SEQUENCE: 16 accaatagt                                                                  9

<210> SEQ ID NO 17
<211> LENGTH: 9
<212> TYPE: DNA
<213> ORGANISM: Artificial
<220> FEATURE:
<223> OTHER INFORMATION: Artificial rabies virus second glycoprotein
      gene sequence of #634-642 of the glycoprotein gene in SPBNGA-GA
      from passage 10

<400> SEQUENCE: 17 accaatagt                                                                  9

<210> SEQ ID NO 18
<211> LENGTH: 9
<212> TYPE: DNA
<213> ORGANISM: Artificial
<220> FEATURE:
<223> OTHER INFORMATION: Artificial rabies virus glycoprotein gene
      sequence of #634-642 of the glycoprotein gene in SPBNGAS from
      passage 0

<400> SEQUENCE: 18 acctccagt                                                                  9

<210> SEQ ID NO 19
<211> LENGTH: 9
<212> TYPE: DNA
<213> ORGANISM: Artificial
<220> FEATURE:
<223> OTHER INFORMATION: Artificial rabies virus glycoprotein gene
      sequence of #634-642 of the glycoprotein gene in SPBNGAS from
      passage 5

<400> SEQUENCE: 19 acctccagt                                                                  9

<210> SEQ ID NO 20
<211> LENGTH: 9
<212> TYPE: DNA
<213> ORGANISM: Artificial
<220> FEATURE:
<223> OTHER INFORMATION: Artificial rabies virus first glycoprotein gene
      sequence of #634-642 of the glycoprotein gene in SPBNGAS-GAS from
      passage 0

<400> SEQUENCE: 20 acctccagt                                                                  9

<210> SEQ ID NO 21
<211> LENGTH: 9
<212> TYPE: DNA
<213> ORGANISM: Artificial
<220> FEATURE:
<223> OTHER INFORMATION: Artificial rabies virus first glycoprotein gene
      sequence of #634-642 of the glycoprotein gene in SPBNGAS-GAS from
      passage 5

<400> SEQUENCE: 21 acctccagt                                                                  9

<210> SEQ ID NO 22
```

```
<211> LENGTH: 9
<212> TYPE: DNA
<213> ORGANISM: Artificial
<220> FEATURE:
<223> OTHER INFORMATION: Artificial rabies virus second glycoprotein
      gene sequence of #634-642 of the glycoprotein gene in SPBNGAS-GAS
      from passage 0

<400> SEQUENCE: 22 acctccagt                                                              9

<210> SEQ ID NO 23
<211> LENGTH: 9
<212> TYPE: DNA
<213> ORGANISM: Artificial
<220> FEATURE:
<223> OTHER INFORMATION: Artificial rabies virus second glycoprotein
      gene sequence of #634-642 of the glycoprotein gene in SPBNGAS-GAS
      from passage 5

<400> SEQUENCE: 23 acctccagt                                                              9

<210> SEQ ID NO 24
<211> LENGTH: 1575
<212> TYPE: DNA
<213> ORGANISM: Artificial
<220> FEATURE:
<223> OTHER INFORMATION: Nucleic acid sequence for the glycoprotein gene
      of rabies virus

<400> SEQUENCE: 24
atggttcctc aggctctcct gtttgtaccc cttctggttt ttccattgtg ttttgggaaa         60
ttccctattt acacgatacc agacaagctt ggtccctgga gtccgattga catacatcac        120
ctcagctgcc caaacaattt ggtagtggag gacgaaggat gcaccaacct gtcagggttc        180
tcctacatgg aacttaaagt tggatacatc ttagccataa agtgaacgg gttcacttgc         240 acaggcgttg tgacggaggc tgaaacctac actaacttcg ttggttatgt cacaaccacg        300
ttcaaaagaa agcatttccg cccaacacca gatgcatgta gagccgcgta caactggaag        360
atggccggtg accccagata tgaagagtct ctacacaatc cgtaccctga ctaccgctgg        420
cttcgaactg taaaaaccac caaggagtct ctcgttatca tatctccaag tgtggcagat        480
ttggacccat atgacagatc ccttcactcg agggtcttcc ctagcgggaa gtgctcagga        540
gtagcggtgt cttctaccta ctgctccact aaccacgatt acaccatttg gatgcccgag        600
aatccgagac tagggatgtc ttgtgacatt tttaccaata gtagagggaa gagagcatcc        660
aaagggagtg agacttgcgg ctttgtagat gaaagaggcc tatataagtc tttaaaagga        720
gcatgcaaac tcaagttatg tggagttcta ggacttagac ttatggatgg aacatgggtc        780
tcgatgcaaa catcaaatga accaaatgg tgccctcccg ataagttggt gaacctgcac        840
gactttcgct cagacgaaat tgagcacctt gttgtagagg agttggtcag gaagagagag        900
gagtgtctgg atgcactaga gtccatcatg acaccaagt cagtgagttt cagacgtctc        960
agtcatttaa gaaaacttgt ccctgggttt ggaaaagcat ataccatatt caacaagacc       1020
ttgatggaag ccgatgctca ctacaagtca gtcgagactt ggaatgagat cctcccttca       1080
aaagggtgtt taagagttgg ggggaggtgt catcctcatg tgaacggggt ttttttcaat       1140
ggtataatat taggacctga cggcaatgtc ttaatcccag agatgcaatc atccctcctc       1200
cagcaacata tggagttgtt ggaatcctcg gttatccccc ttgtgcaccc cctggcagac       1260
```

```
                                              -continued
ccgtctaccg ttttcaagga cggtgacgag gctgaggatt ttgttgaagt tcaccttccc    1320
gatgtgcaca atcaggtctc aggagttgac ttgggtctcc cgaactgggg gaagtatgta    1380
ttactgagtg caggggccct gactgccttg atgttgataa ttttcctgat gacatgttgt    1440
agaagagtca atcgatcaga acctacgcaa cacaatctca gagggacagg gagggaggtg    1500
tcagtcactc cccaaagcgg gaagatcata tcttcatggg aatcacacaa gagtgggggt    1560
gagaccagac tgtaa                                                     1575

<210> SEQ ID NO 25
<211> LENGTH: 318
<212> TYPE: DNA
<213> ORGANISM: Homo sapiens

<400> SEQUENCE: 25
atgggtgatg ttgagaaagg caagaagatt tttattatga agtgttccca gtgccacacc      60
gttgaaaagg gaggcaagca caagactggg ccaaatctcc atggtctctt tgggcggaag     120
acaggtcagg cccctggata ctcttacaca gccgccaata agaacaaagg catcatctgg     180
ggagaggata cactgatgga gtatttggag aatcccaaga agtacatccc tggaacaaaa     240
atgatctttg tcggcattaa gaagaaggaa gaaagggcag acttaatagc ttatctcaaa     300
aaagctacta atgagtaa                                                  318
```

RECOMBINANT RABIES VIRUS COMPOSITIONS

CROSS-REFERENCE TO RELATED APPLICATIONS

This application is the national stage of PCT/US2005/024671 filed Jul. 12, 2005, which claims the benefit of U.S. Provisional Application Ser. No. 60/587,129 filed Jul. 12, 2004, the contents of which are incorporated in this application in its entirety by reference.

GOVERNMENT INTERESTS

The United States Government may have certain rights to this invention pursuant to work funded under grants Phase II SBIR Grant 2 R44 CI0081-02 and by Public Health Service Grants AI45097-6 and AI09706-32.

BACKGROUND

Rabies is a major zoonotic disease that remains an important public health problem, causing 60,000 annual deaths worldwide. In most developing countries, dogs represent the major rabies reservoir, whereas the situation in the Americas is much more complex, since large reservoirs of rabies viruses exist in many wild animal species. In the US, wildlife reservoirs accounted for nearly 93% of the 8,513 reported cases of rabies in 1997. The most frequently reported rabid wildlife species is raccoon (50.5%), followed by skunk (24.0%). Outbreaks of rabies infection in these terrestrial mammals are found in broad geographic areas across the US. For example, raccoon rabies affects an area of more than 1 million square kilometers from Florida to Maine.

Oral immunization of wildlife with live vaccines, such as the modified-live rabies virus vaccines SAD B19, SAG-1, and SAG-2 or the vaccinia-rabies glycoprotein recombinant virus vaccine VRG, is the most effective method to control and eventually eradicate rabies. In the past decade, more than 15 million baits containing VRG have been distributed in the US through programs designed to control rabies among free-ranging raccoons, foxes and coyotes. Since 1997, oral vaccination campaigns in Ohio have led to a highly significant reduction in raccoon rabies without any adverse effects in humans. However, in September 2000, a person who was exposed to VRG during an oral vaccination campaign developed severe local inflammatory reactions. This incident underlines the heightened need for safer live rabies vaccines, particularly as wildlife rabies vaccination efforts in the US intensify on a national level.

SUMMARY

In one embodiment of the invention a non-pathogenic recombinant rabies virus comprising a modified or altered G gene that codes for a glycoprotein of a rabies virus that remains non-pathogenic following one or more passages in an immunoincompetent mammal such as a newborn mammal is provided. The non-pathogenic recombinant rabies may have at least one nucleotide encoding amino acid 194 in the G (glycoprotein) gene that resists mutation. One aspect of the invention provides a non-pathogenic recombinant rabies virus wherein the amino acid 194 of the glycoprotein gene is serine. A further aspect provides a non-pathogenic recombinant rabies virus comprising at least one nucleotide encoding amino acid 194 in the G gene that resists mutation and wherein the recombinant rabies virus expresses two G proteins.

Another aspect of the invention is a non-pathogenic recombinant rabies virus comprising a G gene that expresses a glycoprotein and the G gene has one or more nucleotides that inhibit the G gene from mutating to a pathogenic form. A further aspect is a non-pathogenic recombinant rabies virus comprising a G gene that expresses a glycoprotein and the G gene has one or more nucleotides that inhibit the G gene from mutating to a pathogenic form wherein the G gene expresses a glycoprotein where amino acid 194 is not lysine. In one aspect amino acid 194 is a serine.

An aspect of the invention is also a non-pathogenic recombinant rabies virus comprising a G gene that expresses a glycoprotein and the G gene has one or more nucleotides that inhibit the G gene from mutating to a pathogenic form wherein the G gene expresses a glycoprotein with a glutamic acid at amino acid 333 (GA). A further aspect is a virus with a G gene that expresses a glycoprotein with a serine at amino acid 194 and a glutamic acid at amino acid 333.

An aspect of the invention is also a non-pathogenic recombinant rabies virus comprising a G gene that expresses a glycoprotein, the G gene has one or more nucleotides that inhibit the G gene from mutating to a pathogenic form, and at least one pro-apoptotic gene expressing at least one pro-apoptotic protein. The pro-apoptotic protein can be cytochrome c or an additional GA.

An embodiment of the invention is a composition comprising a non-pathogenic recombinant rabies virus that overexpresses apoptosis inducing proteins and that expresses a glycoprotein where amino acid 194 is not lysine. In one embodiment the apoptosis inducing protein is cytochrome c or GA. In a further embodiment the non-pathogenic recombinant rabies virus in the composition is live.

One embodiment is a pharmaceutical composition comprising an amount of a recombinant rabies virus that induces a protective immune response when administered orally to a mammal, and an acceptable carrier. In one embodiment the pharmaceutical composition includes a modified rabies virus in a concentration greater than about $10^8$ FFU/ml.

One embodiment is a method for making a recombinant rabies virus comprising incubating cells in growth media that is pH and dissolved oxygen controlled, and infecting the cells with infectious recombinant rabies virus particles. The virus titer can be greater than about $5.3 \times 10^8$ FFU/ml.

Another embodiment is a method of making a non-pathogenic recombinant rhabdovirus comprising passaging a recombinant rhabdovirus through a new born mammal; recovering the recombinant rhabdovirus from the mammal; comparing a G gene of the recombinant rhabdovirus to the G gene of a 0 passage recombinant rhabdovirus to identify one or more mutation sites; and performing site mutagenesis to replace one or more nucleotides of a codon at the mutation site in the rhabdovirus gene with one or more nucleotides of a codon that resists mutation.

One embodiment of the invention provides a vaccine comprising a non-pathogenic recombinant rabies virus comprising a G gene that expresses a glycoprotein, the G gene has one or more nucleotides that inhibit the G gene from mutating to a pathogenic form, and a pharmaceutically acceptable carrier. In one embodiment the vaccine may have more than one virus serotype. Further embodiments provide a vaccine that provides protection against infection from one or more street rabies virus strains.

Another embodiment is a method of protecting an animal susceptible to being infected with rabies virus comprising inoculating the animal with an effective amount of the vaccine comprising a non-pathogenic recombinant rabies virus comprising a G gene that expresses a glycoprotein, the G gene has one or more nucleotides that inhibit the G gene from mutating to a pathogenic form, and a pharmaceutically acceptable carrier. In one embodiment the vaccine is administered as a bait at a dose greater than about $10^8$ FFU/ml.

Another embodiment is a recombinant rabies virus having a G gene comprising at least one exchanged nucleotide in at least one codon causing that codon to resist mutation that would result in an amino acid change when passaged through an immunoincompetent mammal such as a newborn mammal providing a non-pathogenic recombinant rabies virus. The rabies virus can have at least one exchanged nucleotide in the codon in the G gene for amino acid 194 of the glycoprotein that causes the codon to resist mutation that would result in an amino acid change after passage through a newborn mammal. In another embodiment the rabies virus can have a G gene that codes for a serine at amino acid 194 of the glycoprotein. The rabies virus may have a G gene that expresses a glycoprotein where amino acid 333 of the glycoprotein is an amino acid which makes the rabies virus non-pathogenic.

The invention further provides embodiments of a non-pathogenic recombinant rabies virus having a G gene comprising at least one exchanged nucleotide in at least one codon that causes the codon to resist mutation that would result in an amino acid change when passaged through a newborn (immunoincompetent) mammal, therein providing a non-pathogenic recombinant rabies virus and comprising a foreign gene expressing a protein antigen. The protein antigen may comprise at least one antigen from a pathogen. An embodiment provides a vaccine comprising a recombinant rabies virus comprising a foreign gene expressing a protein antigen and a pharmaceutically acceptable carrier.

An embodiment of the invention is a method of protecting a human comprising administering an effective amount of the vaccine comprising a recombinant rabies virus having a G gene comprising at least one exchanged nucleotide in at least one codon causing the codon to resist mutation that would result in an amino acid change when passaged through an immunoincompetent mammal, therein providing a non-pathogenic recombinant rabies virus and comprising a foreign gene expressing a protein antigen from a pathogen and a pharmaceutically acceptable carrier and protecting the human against the pathogen.

Another embodiment is a recombinant rabies virus expressing a glycoprotein gene comprising at least one sequence of SEQ ID NO 5. Embodiments of the invention also provide a modified glycoprotein gene comprising SEQ ID NO: 5.

BRIEF DESCRIPTION OF THE FIGURES

The file of this patent contains at least one drawing/photograph executed in color. Copies of this patent with color drawing(s)/photograph(s) will be provided by the Office upon request and payment of the necessary fee.

FIG. 4 Site-directed mutagenesis of amino acid 194 of the RV G protein.

FIG. 5. Schematic presentation of the genome structure of RV recombinant viruses.

FIG. 7. Loss of body weight after infection with recombinant RVs.

FIG. 8. Nucleotide sequence analysis of GA codon for amino acid residue 194 of SPBNGA-S and SPBNGAS-GAS at passage 0 and $5^{th}$ passage in suckling mice.

DESCRIPTION

Figure 1:
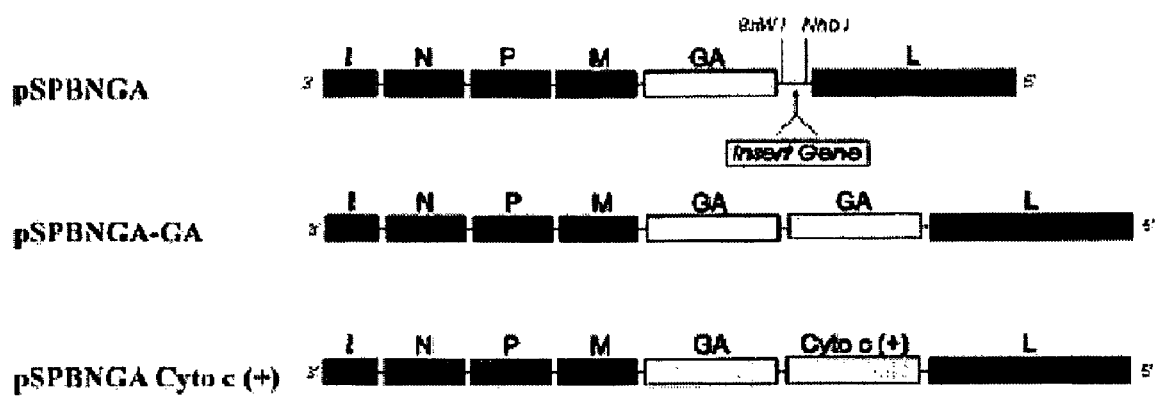
FIG. 1 Schematic diagram of RV recombinant viruses. All three recombinant viruses carry an RV G gene with an Arg333→Glu333 mutation (GA gene). SPBNGA-GA contains the GA gene in duplicate and SPBNGA-Cyto c (+) carries the human cytochrome c gene. I, N, P, M and L indicate the leader sequence, nucleoprotein gene, phosphoprotein gene, membrane protein gene and polymerase gene, respectively.
Figure 2:
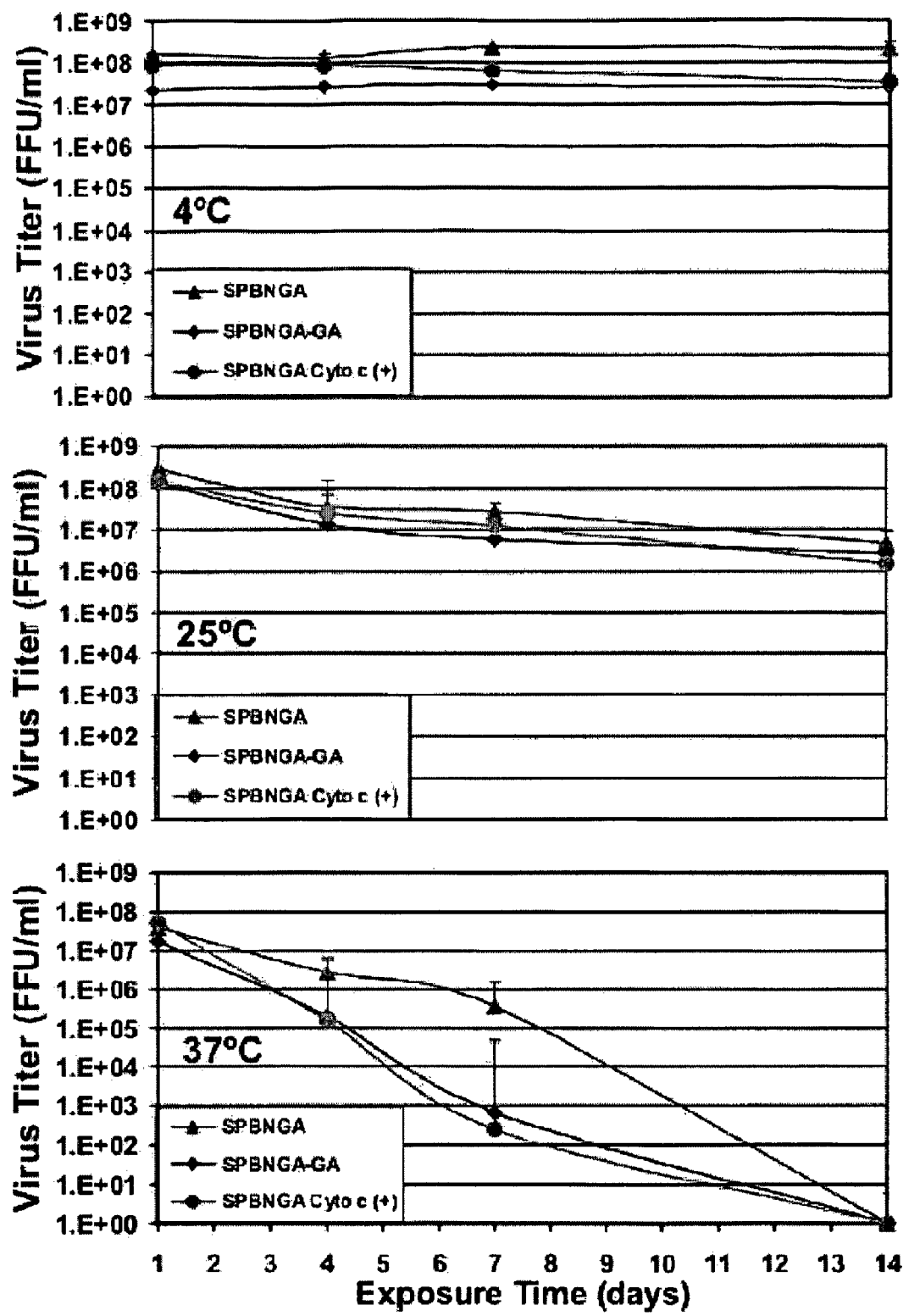
FIG. 2 Thermostability profiles of the recombinant RVs SPBNGA, SPBNGA-GA, and SPBNGA-Cyto c (+). Recombinant RVs produced in bioreactor cultures of BHK cells were incubated for different times at the indicated temperatures and virus titers were determined in triplicate. Data are mean +SE.

Before the present compositions and methods are described, it is to be understood that this invention is not limited to the particular molecules, compositions, methodologies or protocols described, as these may vary. It is also to be understood that the terminology used in the description is for the purpose of describing the particular versions or embodiments only, and is not intended to limit the scope of the present invention which will be limited only by the appended claims.

It must also be noted that as used herein and in the appended claims, the singular forms "a", "an", and "the" include plural reference unless the context clearly dictates otherwise. Thus, for example, reference to a "cell" is a reference to one or more cells and equivalents thereof known to those skilled in the art, and so forth. Unless defined otherwise, all technical and scientific terms used herein have the same meanings as commonly understood by one of ordinary skill in the art. Although any methods and materials similar or equivalent to those described herein can be used in the practice or testing of embodiments of the present invention, the preferred methods, devices, and materials are now described. All publications mentioned herein are incorporated by reference. Nothing herein is to be construed as an admission that the invention is not entitled to antedate such disclosure by virtue of prior invention.

"Optional" or "optionally" means that the subsequently described event or circumstance may or may not occur, and that the description includes instances where the event occurs and instances where it does not.

Embodiments of the present invention provide recombinant non-pathogenic, live rabies viruses that have been modified to prevent or eliminate mutation or revision to a pathogenic form. The amino acid(s) in the G protein of a live rabies virus that result in a pathogenic form of the virus can be determined and the G gene, or more specifically the codon(s) for the one or more amino acids in the G gene, can be modified by exchange of one or more nucleotides. The modified G gene provides for a non-pathogenic live rabies virus that eliminates or resists subsequent mutation resulting in a change of amino acids in the expressed glycoprotein from occurring. Examples of such mutations resulting in a change of amino acid are those that result from passage of the virus in small newborn mammals. The recombinant rabies virus in embodiments of the present invention may be used in pharmaceutical compositions and administered to animals.

One approach to obtaining more potent and safer wildlife RV vaccines is through the use of reverse genetics technology to develop recombinant RVs. To increase the safety and immunogenicity of RV vaccines, distinct genetic alterations that affect the pathogenicity, but not the immunogenicity, of the virus can be introduced into the viral genome. For example, the recombinant RV SPBNGA can be constructed to carry the G gene of SAD B19 in which $Arg_{333}$ is replaced with $Glu_{333}$. The $Glu_{333}$ containing G protein, referred to as GA, renders the virus non-pathogenic for adult mice after intracranial (i.c). infection. $Arg_{333}$ can be replaced with other amino acids which render it non-pathogenic, for example aspartic acid can be used to replace $Arg_{333}$ to form an $Asp_{333}G$ protein. Preferably the amino acid 333 for the G gene of SAD B19 is not arginine in non pathogenic embodiments of the present invention.

$Glu_{333}$ containing recombinant RVs SPBNGA-GA and SPBNGA-Cyto c (+) have been constructed to overexpress the RV G protein or the co-stimulatory pro-apoptotic protein cytochrome c (+), respectively. These recombinant viruses are nonpathogenic for immunocompetent mammals regardless of the route of infection. However, after 10 serial virus passages in newborn mice it was determined that all the viruses had undergone mutation and some had become pathogenic for adult mice. The reversion to the pathogenic phenotype in these particular recombinant non-pathogenic rabies virus involved a thymidine to adenosine mutation (T→A) at position 639 of the G gene, which results in an asparagine to lysine exchange. Other mutations in different rabies virus may also lead to reversion of a non-pathogenic virus into a pathogenic rabies virus. The methods disclosed herein for passaging a virus, identifying a mutated virus containing one or more exchanged amino acids, and modifying one or more G genome nucleotides encoding one or more codons may be applied to other rabies viruses and the present invention is not limited to identifying and preventing a thymidine to adenosine mutation (T→A) at position 639 of the G gene of SPBNGA, SPBNGA-GA, or SPBNGA-Cyto c (+).

One way to prevent an amino acid exchange in a GA protein, for example an Asn →Lys exchange in the GA protein, is that at least one nucleotide from nucleotides 637-639 encoding the amino acid at position 194 of the glycoprotein can be changed by site directed mutagenesis from AAT to for example TCC (resulting in the sequence identified as GAS, SEQ ID NO: 5). This mutation, which replaces asparagine at position 194 in the protein with serine, minimizes the possibility for an Asn →Lys exchange at amino acid position 194 of the G protein. Other degenerate codons for serine may be utilized in a G gene at position 637-639, and other amino acids which minimize the possibility for an Asn→ Lys exchange at amino acid position 194 of the GA protein may have their codon inserted at position 637-639 in the G gene. For a GA protein having for example an amino acid like serine coded for at amino acid position 194, the mutagenized GA protein may be designated as GAS and the recombinant viruses expressing the GAS gene (SEQ ID NO: 5) are termed SPBNGAS, SPBNGAS-GAS, or SPBNGAS-Cyto c.

To confirm that a particular amino acid exchange at a position in the GA or other G protein from the recombinant RVs is responsible for the reemergence of the pathogenic phenotype, the codon for the amino acid of the G gene expressing the GA protein or other G protein can be modified so that the G gene expresses the protein with the exchanged amino acid. The mutagenized G gene can be reintroduced into the SPBN or other vector resulting in recombinant RVs such as SPBNGAXaa which carries the exchanged amino acid Xaa at the exchange position of its GA protein (GAXaa). For example, to confirm that the amino acid change Asn→Lys at position 194 in the GA of the recombinant RV is responsible for reemergence of the pathogenic phenotype, the codon for the amino acid at 194 of the GA gene can be modified so that the GA gene expresses the protein with the Asn→Lys change. The mutagenized GA gene can be reintroduced into the SPBN or other RV vector resulting in recombinant RVs SPBNGAK which carries the exchanged amino acid Lys at position 194 of its GA protein.

The pathogenicity of recombinant RVs containing modified G genes can be determined by injection of the recombinant virus into groups of adult Swiss Webster mice intracranially with about $10^5$ infectious virus particles. After infection with the modified recombinant virus, clinical signs, body weight, and mortality rates can be monitored daily for several weeks or months to determine the pathogenicity of the modified viruses.

Recombinant RVs such as but not limited to SPBNGAS, SPBNGAS-GAS, and SPBNGAS-Cyto c are considerably safer as compared to previously developed recombinant RVs SPBNGA, SPBNGAGA, and SPBNGA-Cyto c, because they all carry the GAS RV G protein which has an additional amino acid exchange that significantly reduces the possibility of these viruses to revert to the pathogenic phenotype.

One possible use of recombinant RVs like SPBNGAS, SPBGAS-GAS, SPBNGAS-Cyto c or others is for the vaccination of wildlife, and in particular vaccination utilizing baits. In addition, these viruses can express foreign protein antigens and therefore have a utility as safe and effective vaccine vectors that can be used for vaccination against many pathogens. Examples include but are not limited to HIV-1 Gag which may be inserted into the G gene of a recombinant rabies virus using the present invention and teaching, of McGettigan et. al. J. Virology, January 2003, pp. 237-244, the disclosure of which is incorporated herein by reference in its entirety. The efficacy and safety of the of recombinant RVs such as but not limited to SPBNGAS, SPBNGAS-GAS, and SPBNGAS-Cyto c in vaccines can be first studied in laboratory mice and then in target animals including dogs, skunks and raccoons.

Serial passaging refers to the infection of a cell line or an animal with a virus isolate, the recovery of the viral progeny from the host cells or animal, and the subsequent infection of fresh host cells or new animals with the viral progeny to generate the next passage.

Administration of the live attenuated viruses disclosed herein may be carried out by any suitable means, including both parenteral injection (such as intraperitoneal, subcutaneous, or intramuscular injection), orally and by topical application of the virus (typically carried in the pharmaceutical formulation) to an airway surface. Topical application of the virus to an airway surface can be carried out by intranasal administration (e.g. by use of dropper, swab, or inhaler which deposits a pharmaceutical formulation intranasally). Topical application of the virus to an airway surface can also be carried out by inhalation administration, such as by creating respirable particles of a pharmaceutical formulation (including both solid particles and liquid particles) containing the virus as an aerosol suspension, and then causing the subject to inhale the respirable particles. Methods and apparatus for administering respirable particles of pharmaceutical formulations are well known, and any conventional technique can be employed. As a result of the vaccination the host becomes at least partially or completely immune to a rabies virus infection.

The vaccine composition containing the attenuated rabies virus in embodiments of the present invention can be administered to an animal susceptible to or otherwise at risk of rabies infection to enhance the individual animal's own immune response capabilities. Such an amount is an immunogenically effective dose. The virus may be live or killed. In this use, the precise amount again depends on the subject's state of health and weight, the mode of administration, the nature of the formulation, etc. Preferably the amount of attenuated or non-pathogenic live rabies virus in order to achieve sufficient immunoprotection (an immunogenically effective dose) should be an amount that the vaccine virus should be able to replicate sufficiently in the recipient so that enough viral antigen is presented to the immune system. Methods useful for characterizing effective amounts of non-pathogenic virus in a vaccine as well as rabies viruses which may be modified are disclosed by Dietzschold et. al. in PCT Application WO 01/70932 the contents of which are incorporated herein by reference in their entirety. Other methods and materials useful in the practice of embodiments of the present invention can include those described in U.S. Pat. Application Pub. No. 2002/0131981 the contents of which are incorporated herein by reference in their entirety. The amount of recombinant virus can be about $10^4$ FFU/ml or greater, preferably $10^6$ FFU/ml or greater. For use in baits, the amount of live recombinant virus is preferably greater than $10^6$ FFU/ml, more preferably $10^8$ FFU/ml or greater. The vaccine formulations preferably provide a quantity of attenuated rabies virus of the invention sufficient to effectively protect the subject against serious or life-threatening rabies virus infection.

The non-pathogenic rhabdovirus including a modified G gene that resists mutation to a pathogenic form of the virus may be live or killed. Sufficiently high doses of a single, non-pathogenic live recombinant rabies virus of the present invention can be administered to an animal providing protection against infection by all of the street rabies virus strains that are associated with different mammalian species in a diverse geographical location.

Methods and compositions of the present invention can confer clinical benefits to the treated mammals, providing clinically relevant titers against RV as measured for example by serum neutralization of RV followed by infection of mouse neuroblastoma cells and detection of infected cells with direct immunofluorescence antibody technique.

RV activity can be stabilized by the addition of excipients or by lyophilization. Stabilizers may include carbohydrates, amino acids, fatty acids, and surfactants and are known to those skilled in the art. Stabilizers may be used to improve the thermal stability of the recombinant viruses, especially for temperatures at or above about 37° C.

Live or killed viruses of the present invention may be administered topically, orally i.c. or i.m. or locally or systemically. Oral administration using vaccines with bait can be used for treating wild or stray animals. The attenuated or non-pathogenic live rabies viruses, singularly or in combination, can be mixed with an appropriate pharmaceutical carrier prior to administration. Examples of generally used pharmaceutical carriers and additives are conventional diluents, binders, lubricants, coloring agents, disintegrating agents, buffer agents, isotonizing agents, preservants, anesthetics and the like. Pharmaceutical carriers that may be used are dextran, sucrose, lactose, maltose, xylose, trehalose, mannitol, xylitol, sorbitol, inositol, serum albumin, gelatin, creatinine, polyethylene glycol, non-ionic surfactants (e.g. polyoxyethylene sorbitan fatty acid esters, polyoxyethylene hardened castor oil, sucrose fatty acid esters, polyoxyethylene polyoxypropylene glycol) and similar compounds.

Pharmaceutical carriers may also be used in combination, such as polyethylene glycol and/or sucrose, polyoxyethylene sorbitan fatty acid esters, or polyoxyethylene sorbitan monooleate.

The suitability of recombinant rabies vaccines for wildlife or use as vectors for vaccination depends, in part, on the preservation of virus infectivity even after extended exposure to a wide range of temperatures. To determine if the addition of a foreign gene (e.g. cytochrome c) or the duplication of the RV G gene, or modification of a G gene codon impairs the stability of the recombinant RVs, the viral titers of the recombinant viruses can be determined after different times of exposure to different temperatures. To obtain information on vaccine stability in a short period of time, the tests can be performed in absence of added virus stabilizers. Alternatively the stability of recombinant viruses in different stabilizers can be assessed.

Quantities of the mutation resistant or modified G gene recombinant viruses such as but not limited to SPBNGAS, SPBNGA-GAS, SPBNAGAS-GA, SPBNGAS-GAS, and SPBNGAS-Cyto c (+) can be prepared in a stirred tank bioreactor with cultures of various cells including but not limited to BHK or BSR cells. Recombinant viruses such as SPBNGA and SPBNGA-Cyto c(+) can also be prepared by this method. Preferably quantities of the recombinant viruses are prepared in a stirred tank bioreactor with BSR cells. Bioreactor-produced vaccine lots can be tested for their thermostability, immunogenicity, pathogenicity, and genetic stability in newborn mice.

A stirred tank reactor equipped with a fibrous bed basket on which cells grow can be used. The bioreactor can be seeded with about $10^8$ BHK or BSR cells suspended in MEM (MEDIATECH) supplemented with 10% fetal bovine serum, and incubated for several days at about 37° C. in batch mode. The reactor is preferably perfused with a mixture of oxygen, nitrogen, carbon dioxide at a rate to maintain the temperature, pH, and dissolved oxygen content (DO)Of the medium. The composition of the gases can be monitored and controlled to maintain a pH of about 7 and a DO (dissolve oxygen) of about 37% throughout the incubation period.

For virus production in BSR cells, the growth medium can be removed and replaced with medium such as but not limited to OptiPro™ SFM supplemented with 4 mM glutamine and for BHK cells, growth medium can be replaced with but not limited to MEM containing 0.2% bovine serum albumin. In both cases, replacement medium contained about $10^8$ infectious virus particles. After infection, incubation temperature and pH can be decreased to about 34° C. and 6.8, respectively, and the DO maintained at about 37%, and the incubation continued for several days and up to a week or more. Killed viruses can be prepared, for example, by adding β-propiolactone to a final concentration of 0.5% BPL at neutral pH for 2 hours at 4° C.

Various aspects of the present invention will be illustrated with reference to the following non-limiting examples.

EXAMPLE 1

Materials and Methods for modifying the RV G protein gene can include those disclosed in U.S. application Ser. No. 10/268,197, now U.S. Pat. No. 7,223,584, the contents of which are incorporated herein by reference in its entirety.

Mice: Four to six-week-old female Swiss Webster mice or pregnant Swiss Webster mice were purchased from Taconic (Germantown, N.Y.).

Cells and viruses: BHK 21 cells and a subclone (BSR), were grown in MEM medium (MEDIATECH, INC. Herndon, Va.) supplemented with 10% fetal bovine serum. Mouse NA neuroblastoma cells were grown in RMPI medium (MEDIATECH) supplemented with 10% fetal bovine serum.

Construction of the recombinant RVs SPBNGA, SPB-NGA-Cyto c (+), and SPBNGA-GA have been described. FIG. 1 shows these three virus constructs schematically. SPB-NGA is the empty RV vector and expresses a single GA gene (SEQ ID NO: 24), SPBNGA-GA contains an extra RV G gene and expresses two GA genes (two of SEQ ID NO: 24), and SPBNGA-Cyto c (+) expresses the contains the human cytochrome c gene (SEQ ID NO: 25).

Virus production: For virus production in stationary cell cultures, monolayers of BHK 21 or BSR cells were infected with the different recombinant RVs at m.o.i. of 0.1. After 1-h incubation at 37° C., the inoculum was removed and BSR cells were replenished with OptiPro SFM medium (Invitrogen, Grand Island, N.Y.) supplemented with 4 mM glutamine, while BHK cells were replenished with MEM containing 0.2% bovine serum albumin. Infected cells were incubated for 3 days at 34° C.

For virus production in bioreactor, the 2.2 L-CelliGen Plus Universal Stirred Tank bioreactor System (New Brunswick Scientific Co., New Brunswick, N.J.), equipped with a fibrous bed basket containing 70 g NBS Fibra-Disks on which cells grow, was used. The bioreactor was seeded with $3.75 \times 10^8$ BHK or BSR cells suspended in 1.3 L of MEM (MEDIATECH) supplemented with 10% fetal bovine serum, and incubated for 3 days at 37° C. in batch mode. The reactor was perfused with a mixture of oxygen, nitrogen, carbon dioxide at a constant rate of 0.2 L/min, and the composition of the gases was constantly monitored and computer-controlled to maintain a pH of 7.0 and a DO (dissolve oxygen) of 37% throughout the incubation period. For virus production in BSR cells, the growth medium was removed and replaced with medium OptiPro SFM supplemented with 4 mM glutamine and for BHK cells, growth medium was replaced with MEM containing 0.2% bovine serum albumin. In both cases, replacement medium contained $2.5 \times 10^8$ infectious virus particles. After infection, incubation temperature and pH were decreased to 34° C. and 6.8, respectively, and the DO was kept at 37%, and incubation was continued for 6 days.

Virus infectivity assay: Infectivity assays were performed at 34° C. on monolayers of NA cells in 96-well plates. All titrations were carried out in triplicate.

Thermostability test: Samples of the three different recombinant viruses produced in bioreactor using BHK cells were incubated for 1, 4, 7, and 14 days at 4° C., 25° C., and 37° C. without addition of stabilizers and virus titers were determined as described above.

Infection of mice: Newborn Swiss Webster mice were injected i.c. with $10^4$ infectious virus particles in 5 ml PBS. One litter of 8 to 15 mice was used for each virus. Three days post-infection, mice were euthanisized with $CO_2$ and brains were removed and homogenized in 4 volumes (ml/g) of PBS. The brain homogenate was clarified by centrifugation, and aliquots were stored at −80° C.

Adult mice were anesthetized with isofluorane and infected i.c. with $10^5$ infectious RV particles in 10 ml PBS. Mice were observed for 30 days for clinical signs of rabies; brains of mice that died or that survived the infection were removed and RNA was isolated from brain tissue as described below.

RNA isolation, RT PCR, and nucleotide sequence analysis: To isolate RNA from cell cultures, BHK or BSR cells grown in T25 tissue culture flasks were washed with PBS and RNA was extracted using RNeasy Mini Kit (Qiagen, Valencia, Calif.) according to the manufacturer's protocol. To isolate RNA from mouse brain tissue, brains were removed, snap-frozen and homogenized in TRI Reagent (Sigma, St. Louis, Mo.) at a ratio of 1:10; after adding 200 ml of chloroform to 1 ml of homogenate, samples were incubated at room temperature for 10 min, centrifuged for 15 min at 12,000 rpm at 4° C., the aqueous phase was collected, and RNA was isolated using the RNeasy Mini Kit as above.

For synthesis of RV G cDNA, Superscript One-Step RT-PCR (Invitrogen, Carlsbad, Calif.) and primers SADB19–120seq(+) (AAC ATG TTA TGG TGC CAT TAA ACC GCT, (SEQ ID NO: 1) and SADB19+50seq(−) (GGG TGT TAG TTT TTT TCA TGG ACT TGG, (SEQ ID NO: 2) were used. To synthesize cytochrome c cDNA from SPBNGA-Cyto c (+) or RV G cDNA from the second G gene of SPBNGA-GA, primers SBsi2seq(+) (TAA TTA ACG TCC TTT CAA CGA TCC, (SEQ ID NO: 3) and SNhe2seq(−) (GAG CAT CTT GAA GTA AGT AGT CTC AGG, T (SEQ ID NO: 4) were used. PCR-amplified products were subjected to nucleotide sequencing and the complete nucleotide sequences of the G gene(s) (SEQ ID NO: 24) or cytochrome c gene (SEQ ID NO: 25) were obtained and analyzed for presence of mutations.

Comparison of recombinant virus production in stationary and bioreactor cultures of BHK and BSR cells. To investigate whether the oral vaccine candidates can be produced at sufficiently high concentrations the recombinant RVs SPBNGA, SPBNGA-GA, and SPBNGA-Cyto c (+) were grown in stationary and bioreactor cultures of BHK and BSR cells. Maximum virus titers reaching levels of $1 \times 10^{10}$ FFU/ml for SPBNGA, $9.3 \times 10^9$ for SPBNGA-GA, and $5.3 \times 10^8$ for SPBNGA-Cyto c (+) were obtained using BSR cells and bioreactor technology (Table 1). These titers are on average 37 to 66-fold higher than those produced in stationary cultures and are also higher (P=0.01) than those obtained in bioreactor-grown BHK cultures. The production of similar amounts of virus in stationary cultures would require 1000 T175 flasks and 30 liters of medium. Without wishing to be bound by theory, the high titers of RV in the Bioreactor system may be the relatively higher cell density that is maintained due to the control of nutrients, dissolved oxygen levels, temperature and pH as described.

TABLE 1

Virus titers produced in BioReactor and stationary culture of BHK and BSR cells.

| Vaccine | Method of Virus Production* Virus Titer (FFU/ml) | | | |
|---|---|---|---|---|
| | Bioreactor Culture | | Stationary Culture | |
| Virus Strain | BSR cells | BHK cells | BSR cells | BHK cells |
| SPBN-GA | $1.0 \times 10^{10}$ | $4.3 \times 10^9$ | $1.5 \times 10^8$ | $4.5 \times 10^9$ |
| +/−Standard Error | $+/−2.1 \times 10^9$ | $+/−1.0 \times 10^9$ | $+/−1.1 \times 10^8$ | $+/−5.0 \times 10^8$ |

TABLE 1-continued

Virus titers produced in BioReactor and stationary culture of BHK and BSR cells.

| Vaccine | Method of Virus Production* Virus Titer (FFU/ml) | | | |
|---|---|---|---|---|
| | Bioreactor Culture | | Stationary Culture | |
| Virus Strain | BSR cells | BHK cells | BSR cells | BHK cells |
| SPBNGA-GA | $9.3 \times 10^9$ | $1.0 \times 10^9$ | $2.5 \times 10^8$ | $9.0 \times 10^8$ |
| +/−Standard Error | $+/−2.6 \times 10^9$ | $+/−0.0 \times 10^9$ | $+/−5.0 \times 10^7$ | $+/−1.0 \times 10^8$ |
| SPBNGA-Cyto c(+) | $5.3 \times 10^8$ | $4.8 \times 10^8$ | $1.4 \times 10^8$ | ND |
| +/−Standard Error | $+/−6.3 \times 10^7$ | $+/−6.3 \times 10^7$ | $+/−2.5 \times 10^7$ | |

ND—not done
*Viruses were harvested 5 days p.i. And virus titers were determined in triplicate The three live rabies virus (RV) recombinant vaccine candidates, SPBNGA, SPBNGA-Cyto c (+), and SPBNGA-GA, were examined for their production levels and stability. Maximum production levels up to $10^{10}$ infectious particles/ml were achieved using bioreactor technology. All virus lots exhibited thermostability profiles typical for RV vaccines and were nonpathogenic for intracranially inoculated immunocompetent mice. Moreover, sequence analysis indicated high genetic stability of the additional gene (the second GA and cytochrome c) in all three RVs during 10 consecutive passages in newborn mice. This analysis revealed no change in the extra RV G gene (SEQ ID NO: 24) in the SPBNGA-GA vaccine or in the cytochrome c gene (SEQ ID NO: 25) in the SPBNGA-Cyto c (+) vaccine. Moreover, no changes were detected in the G gene codon for $Glu_{333}$, which renders the virus nonpathogenic. However, after the 5th passage, a mutation resulting in an $Asn_{194} \rightarrow Lys_{194}$ exchange emerged in the first G genes of all three RVs (FIG. 3, SEQ ID NOS: 7, 10, and 13). This mutation was associated with a modest increase in pathogenicity in SPBNGA and SPBNGA-Cyto c (+), but not in SPBNGA-GA , which contained the mutation in only one of its two G genes (compare SEQ ID NOS: 13-14 for the first GA to SEQ ID NOS: 16-17 for the second GA of SPBNGA-GA) and which remained nonpathogenic.

Thermostability of recombinant virus vaccines. The suitability of vaccines for wildlife depends, in part, on the preservation of virus infectivity even after extended exposure to a wide range of temperatures. To exclude the possibility that the addition of a foreign gene (e.g. cytochrome c) or the duplication of the RV G impairs the stability of the recombinant RVs, the viral titers of the three different viruses were determined after different times of exposure to different temperatures. To obtain information on vaccine stability in a short period of time the tests were performed in absence of added virus stabilizers. As shown in FIG. 2, titers of all three virus lots remained unchanged after 2 weeks of exposure at 4° C., whereas exposure at 25° C. was associated with a decline in titers of all three viruses by 1 log after 1 week and by 2 logs after 2 weeks exposure. After exposure for 4 days at 37° C., titers of SPBNGA decreased by 1 log and those of SPBNGA-GA and SPBNGA-Cyto c (+) decreased by 2 logs; no infectivity was detected in any of the three virus lots after 14 days exposure at 37° C.

Genetic stability of recombinant virus vaccines: A potential problem associated with the use of live recombinant RVs for wildlife immunization rests in the high mutation rate characteristic of RNA viruses. Because the RV G protein is a major marker for RV pathogenicity, the complete sequence of the RV G was analyzed. In addition, the entire sequence of cytochrome c (SEQ ID NO: 25) was determined because the expression of this protein enhances the immunogenicity of this recombinant RV. In the first step, each of the three recombinant viruses was passaged ten times in newborn mice. Immunoincompetent mammals like newborn mice were used because the recombinant RV vaccine candidates in embodiments of the present invention are rapidly cleared after i.c. inoculation into immunocompetent adult animals, making the recovery of virus or viral RNA from these animals unreasonable. RT-PCR and nucleotide sequencing of the G genes (SEQ ID NO: 24) inserted into the vector SPBNGA-GA and cytochrome c gene (SEQ ID NO: 25 ) inserted into the vector SPBNGA-Cyto c (+) recovered from the 5th and 10th passages revealed no mutations in the duplicated G gene or the cytochrome c gene. Furthermore, no exchanges in the GAG codon encoding $Glu_{333}$ were detected in any of the G genes of the three RVs. However, comparison of the nucleotide sequences of the G genes of SPBNGA (SEQ ID NOS: 7-8, FIG. 3A) and SPBNGA-Cyto c (+) (SEQ ID NOS: 10-11, FIG. 3B) and the first G gene of SPBNGA-GA (SEQ ID NO: 13-14, FIG. 3C) from the 5th and 10th passage with the corresponding sequences of the 0 passage of these viruses (SEQ ID NOS: 6, 9, and 12, respectively) revealed a single mutation in codon 637-639 from AAT ($Asp_{194}$ to AAG or AAA ($Lys_{194}$). By contrast, no mutation was detected in the second (inserted) G gene of SPBNGA-GA, even after the 10th mouse passage (SEQ ID NOS: 16-17, FIG. 3D).

Effect of the $Asn_{194} \rightarrow Lys_{194}$ mutation in the RV G gene on pathogenicity: To examine whether the $Asn_{194} \rightarrow Lys_{194}$ mutation in the RV G gene results in an increase in pathogenicity, groups of ten immunocompetent mice were infected i.c. with the RVs from passages 0 and 10. Control mice were infected i.c. with SPBN, which contains a G gene with an $Arg_{333}$ and is therefore lethal for adult mice after i.c. infection. Whereas all mice infected with the O-passage of SPBNGA, SPBNGA-GA, and SPBNGA-Cyto c (+) survived the infection without signs of morbidity, one of ten mice (10%) infected with SPBNGA and four often mice (40%) infected with SPBNGA-Cyto c (+) from the 10th mouse passage succumbed to RV infection (Table 2), as confirmed by RT PCR of brain tissue. None of the mice infected i.c. with SPBNGA-GA from the 10th mouse passage died or showed signs of morbidity. By contrast 90% of the control mice infected i.c. with SPBN died from rabies. RT PCR detected no viral RNA in the brains of non-infected control mice or mice that survived 30 days post-infection.

TABLE 2

Mortality of recombinant RV's from the 0 passage and the 10th newborn mouse passage.

| Virus Stock | Mortality (%)* | |
|---|---|---|
| | 0 Passage | 10th Mouse Passage |
| SPBNGA | 0/10 (0%) | 1/10 (10%) |
| SPBNGA-GA | 0/10 (0%) | 0/10 (0%) |
| SPBNGA Cyto c(+) | 0/10 (0%) | 4/10 (40%) |

*Mice were infected intracerebrally with 10$^4$ FFU and observed for 30 days for appearance Based on the finding that RV-mediated apoptosis results in a strong increase in immunogenicity coupled with a marked reduction in pathogenicity, recombinant RVs that either overexpress the RV G protein (SPBNGA-GA) or express the pro-apoptotic protein cytochrome c (SPBNGA-Cyto c (+) were made. Mice immunized with SPBNGA-GA or SPBNGA-Cyto c (+) showed substantially higher RV-neutralizing antibody titers, which were paralleled by an up to 20-fold increase in protective immunity as compared to mice immunized with the empty vector SPBNGA. A similar high RV-neutralizing antibody titers including up. to 20-fold increase in protective immunity as compared to mice immunized with the empty vector SPBNGA can be achieved with recombinant RV's such as but not limited to SPBNGAS-GAS or SPBNGAS-Cyto c (+). To serve immunization of wildlife, these new recombinant RVs preferably produce high virus titers in cell cultures to ensure economic production, exhibit adequate thermostability, remain nonpathogenic regardless of the route of infection, and are genetically stable precluding reversion to virulence.

Complete delivery of the vaccine dose to wildlife can be difficult, high virus concentrations (>10$^8$ FFU/ml) can be important for successful immunization via vaccine loaded baits. Very high virus concentrations (up to 10$^{10}$ FFU/ml) can be obtained using bioreactor technology and BSR cells. The production of such high virus titers is particularly significant for oral vaccination of stray dogs and skunks, which require much more virus than do foxes, raccoons, or coyotes. The efficient growth of BSR cells in serum-free medium and the absence of pathogens as determined by transmission electron microscopy of the master cell bank (BioReliance, Rockville, Md.) makes these cells especially suitable for production of live recombinant RV vaccines.

The presence of an additional G gene such as, but not limited to, GA (SEQ ID NO: 24) or a foreign gene such as, but not limited to, cytochrome c (SEQ ID NO: 25) does not appear to have a major effect on the thermostability of the virus. Sizable decreases in infectivity associated with the presence of extra genes were observed only at elevated temperatures (e.g., 37° C.). It should be noted that the thermostability of the RVs was analyzed in the presence of serum-free medium without any stabilizers; vaccines used for wildlife immunization may be formulated with stabilizers that can substantially increase the stability of the virus even at elevated temperatures.

None of the three experimental vaccines caused morbidity or mortality in i.c-infected mice. Thus, with respect to pathogenicity, these recombinant RVs meet the WHO standard that modified-live viruses be non-pathogenic for adult mice after i.c. infection.

Sequence analysis of the entire G gene or cytochrome c gene confirmed the genetic stability of the recombinant RVs with respect to the additional genes. No changes were detected in the codon for $Glu_{333}$ of the G gene, which is the major pathogenicity marker, even after ten consecutive newborn mice passages. The high conservation of the genotype of the RV G, which has also been previously reported for other recombinant RVs, is remarkable considering the high mutation frequency of RNA viruses. However, one mutation resulting in an $Asn_{194} \rightarrow Lys_{194}$ exchange was detected in the original G gene of all three RVs after the 5th mouse passage, and increased pathogenicity was observed in two of the three recombinant RVs after the 10th passage. Without wishing to be bound by theory, this implies that the $Asn_{194} \rightarrow Lys_{194}$ mutation could underlie the reemergence of a pathogenic phenotype. The finding that SPBNGA-GA with an $Asn_{194} \rightarrow Lys_{194}$ mutation only in the first G gene remained non-pathogenic indicates that the second G gene has no disadvantages by doubling the possibility for the emergence of pathogenic revertants. In contrast, the second G gene (SEQ ID NO: 24) in SPBNGA-GA, may have actually some preventive effects against expression of the pathogenic phenotype. In this context, it has previously been shown that SPBNGA-GA exhibits increased pro-apoptotic properties, which in turn are associated with a decrease in the pathogenicity of RV.

Oral administration of SPBNGA-GA protects dogs against a lethal RV infection. That finding, together with the ability to produce high virus titers and the lack of pathogenicity for immunocompetent mice even after ten newborn mice passages makes the recombinant RV SPBNGA-GA an excellent candidate for immunization of stray dogs and wildlife.

EXAMPLE 2

Generation and Characterization of SPBNGA Variants Site-Directed Mutagenesis of the Asn Residue at Position 194 of GA To confirm that the Asn→Lys exchange at position 194 in the GA of the recombinant RVs SPBNGA and SPBNGA-Cyto c is responsible for the reemergence of a pathogenic phenotype, the codon AAT for $Asn_{194}$ of GA was exchanged for an AAG which encodes $Lys_{194}$. Furthermore, to minimize the possibility for a mutation to $Lys_{194}$, the AAT codon for $Asn_{194}$ was changed to TCC, resulting in a replacement of $Asn_{194}$ with $Ser_{194}$. The mutagenized GA genes were reintroduced into the SPBN vector resulting in recombinant RVs SPBNGAK which carries a Lys at position 194 of its GA, and recombinant RV SPBNGAS which carries a Ser at position 194 of its GA.

Pathogenicity of recombinant RVs containing mutagenized GA genes. To determine whether the exchange of $Asn_{194}$ in GA to $Lys_{194}$ or $Ser_{194}$ affects the pathogenicity of the viruses, groups of adult Swiss Webster mice were injected intracranially with 10$_5$ infectious virus particles of SPBNGAN (which contains the original GA with an $Asn_{194}$), SPBNGAK, and SPBNGAS. After infection, clinical signs, body weight, and mortality rates were monitored daily for a period of 4 weeks.

TABLE 3

Morbidity and mortality of mutagenized recombinant RV

| Virus | Mortality Rate | % loss body weight | clinical signs score |
|---|---|---|---|
| SPBNGAN | 0/17 | 3 ± 0.2 | 0 |
| SPBNGAK | 2/17 | 15 ± 3 | 1.4 ± 0.1 |
| SPBNGAS | 0/17 | 2 ± 0.1 | 0 |

Table 3 shows that mice infected with SPBNGAK developed clinical signs of rabies (average score 1.4 of a 1-4 scale), lost substantial body weight (~15%), and 2 out of 17 mice (~12%) succumbed to the infection. In contrast, mice infected with SPBNGAN and SPBNGAS exhibited only minor loss of body weight, developed no clinical signs, and none of the infected mice died. These data support that the Asn→Lys exchange at position 194 of GA which occurred during the virus passaging in suckling mice is associated with the emergence of the pathogenic phenotype. The $Asn_{194}$→$Ser_{194}$ in SPBNGAS did not cause an increase in pathogenicity. Moreover, because all 3 bases in the $Ser_{194}$ codon are different from the $Lys_{194}$ codon, the emergence of a pathogenic $Lys_{194}$ variant from SPBNGAS is in contrast to SPBNGAN not expected.

EXAMPLE 3

Generation and Characterization of Recombinant RV Vaccines SPBNGAS and SPBNGAS-GAS Site-directed mutagenesis of the GA gene (SEQ ID NO: 24) and construction of new recombinant RVs. To investigate whether the Asn→Lys mutation resulted in the increase in pathogenicity, site-directed mutagenesis was used to modify the gene by exchanging $Asn_{194}$ with $Lys_{194}$. In an attempt to stabilize the non-pathogenic phenotype, $Asn_{194}$ was also changed to $Ser_{194}$. These mutations are illustrated in FIG. 4. The new recombinant RVs were designated as SPBNGAK, which has a Lys at position 194 of GA, and SPBNGAS, which has a Ser at position 194 of GA. Similarly, these mutations were also introduced into both GA genes of SPBNGA-GA resulting in SPBNGAS-GAS and SPBNGAK-GAK. FIG. 5 shows a schematic drawing of the different recombinant RV constructs.

Figure 6:
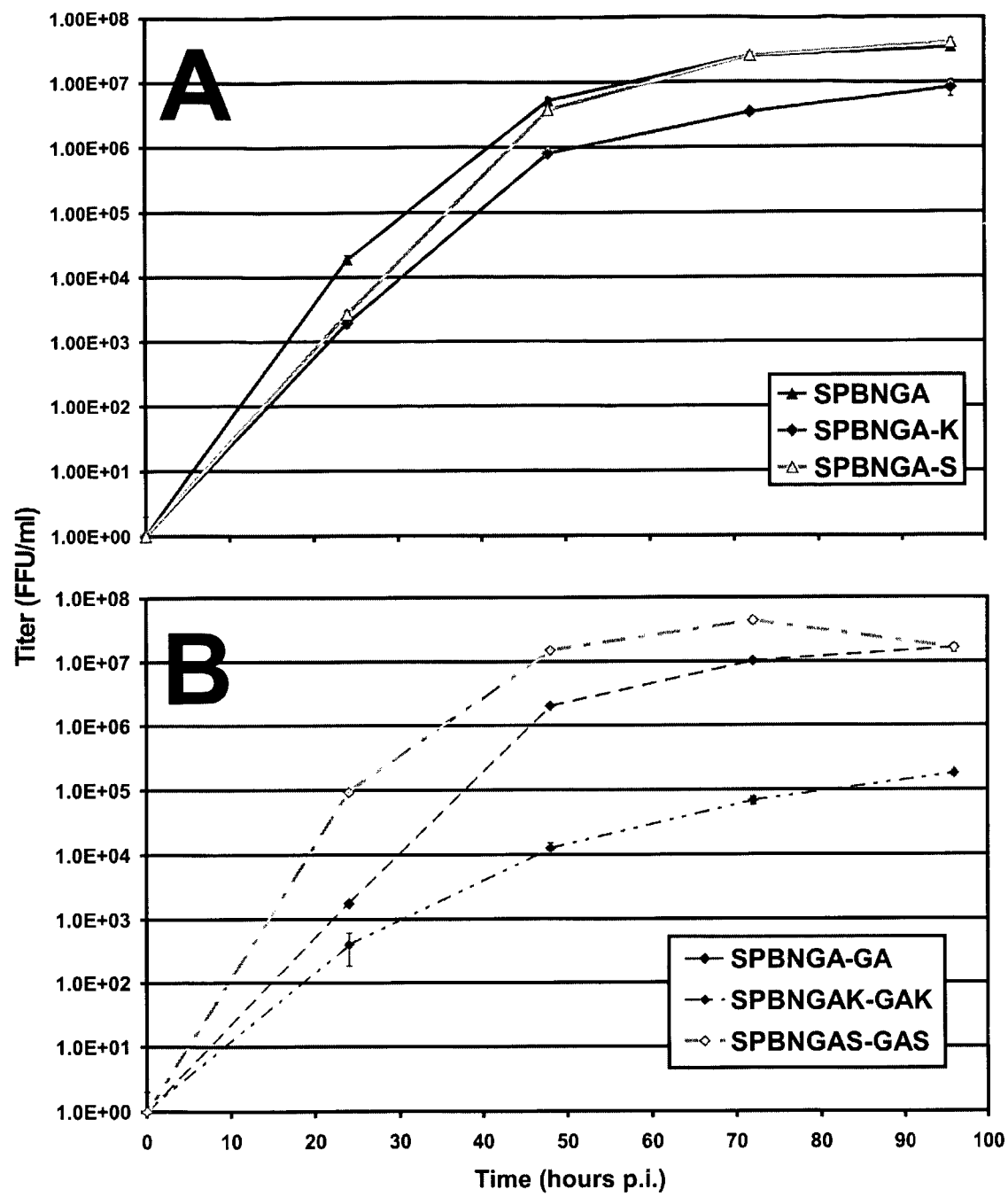
FIG. 6. Multi-step growth curves of single (A) and double (B) glycoprotein RV recombinant viruses.

Characterization of the 194 GA recombinant RVs. The effect of mutations of residue 194 of GA on RV replication in vitro were performed. Multi-step growth curves of single (FIG. 6A) and double (FIG. 6B) glycoprotein containing recombinant RVs in NA cells revealed that the replication rates of SPBNGAK and SPBNGAK-GAK are 1 or 2 logs, respectively, lower than that of SPBNGA or SPBNGA-GA. In contrast, SPBNGAS and SPBNGAS-GAS have similar replication rates to SPBNGA and SPBNGA-GA, indicating that the Asn→Ser mutation in SPBNGAS or SPBNGAS-GAS does not affect the capacity of these viruses to replicate in tissue culture.

Figures 7, 8:
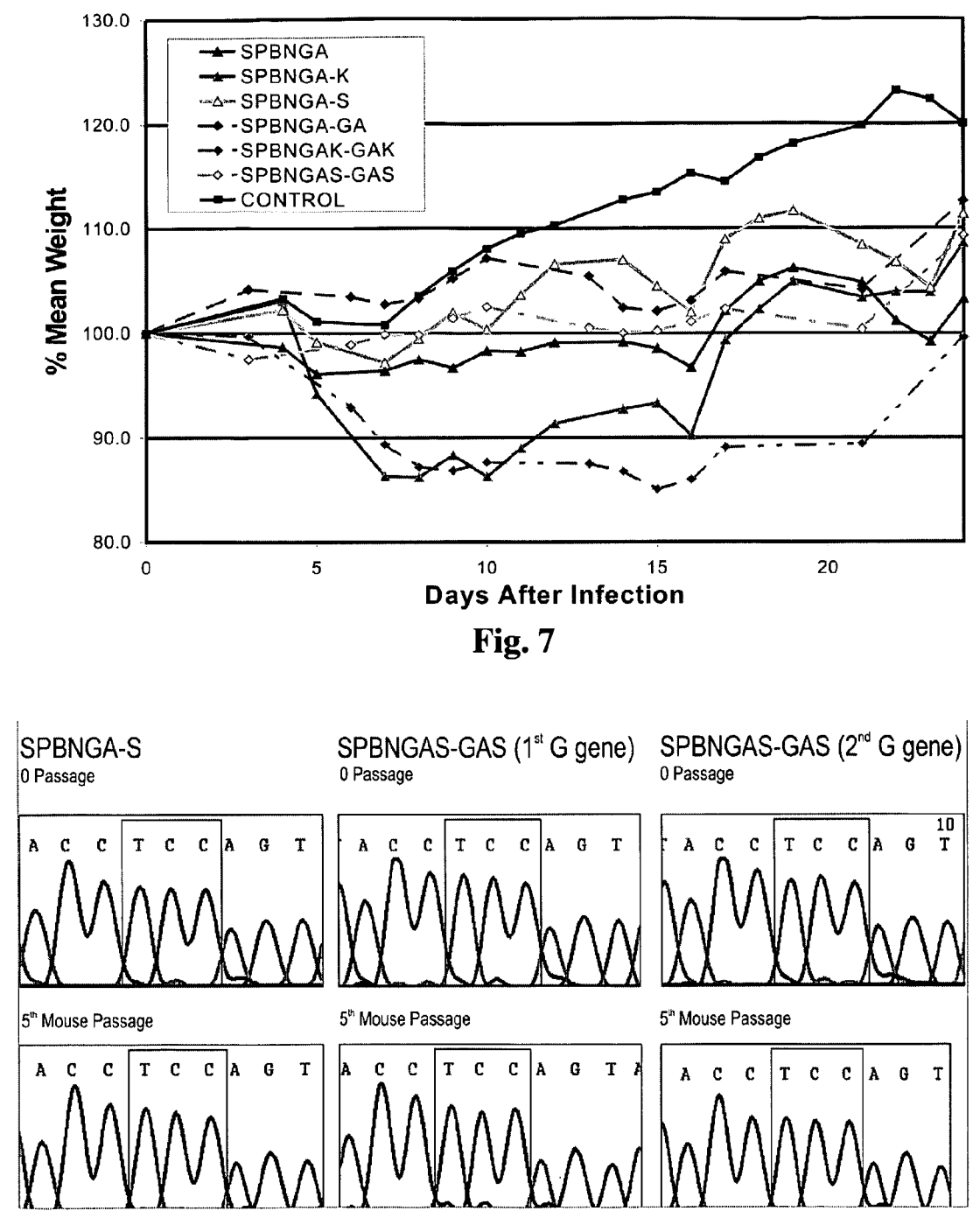

Pathogenicity of RV 194 variants. To determine whether the mutations of amino acid residue 194 of GA affect the outcome of a rabies virus infection in vivo, SPBNGA, SPBNGAK, SPBNGAS, SPBNGA-GA, SPBNGAK-GAK, and SPBNGAS-GAS were administered intracranially (i.c.) to adult female Swiss Webster mice. Mice infected i.c. with $10^6$ FFU of SPBNGAK or SPBNGAK-GAK showed signs of neurological disease, exhibited significant loss of body weight, and 20% and 10%, respectively, of these mice died. In contrast, of all mice infected i.c. with the same FFU of SPBNGA, SPBNGA-GA, SPBNGAS, and SPBNGAS-GAS survived the infection, showed no signs of disease and only minimal loss of body weight (FIG. 7, Table 5).

Figure 3:
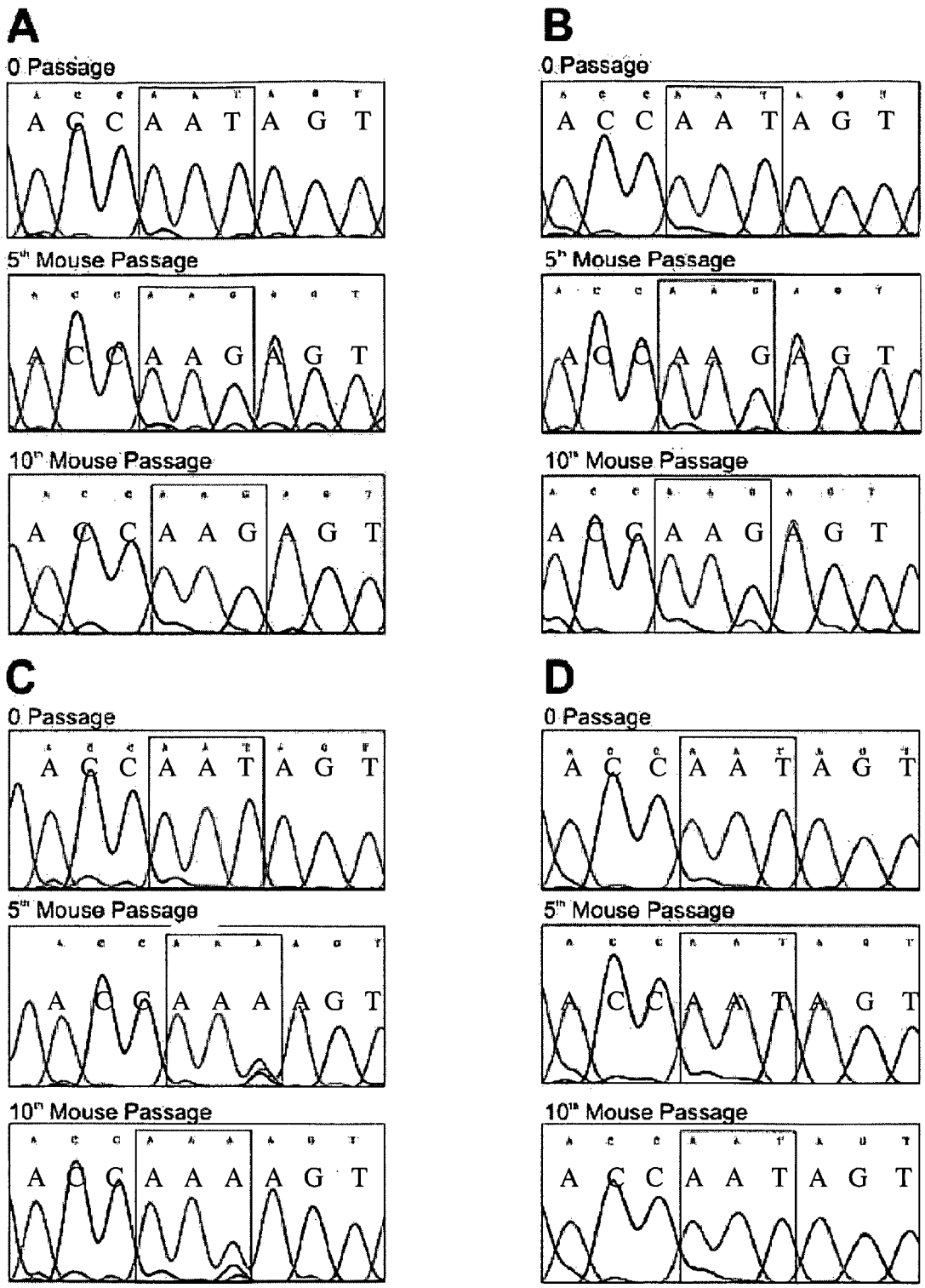
FIG. 3 Sequence of nucleotides 637 to 649 of the RV G genes of SPBNGA (A), SPBNGA-Cyto c (+) (B), and the first (C) and second (D) G gene of SPBNGA-GA. Sequence analysis was performed with viruses (bioreactor production lots), from passage 0, 5 and 10 in newborn mice. The codon for Asn194 or Lys194 is boxed in each panel.

No mortality was observed in mice infected with an SPBNGA-GA that contained the Asn→Lys mutation in only one of the two GA genes (FIG. 3C, first GA, fifth passage (SEQ ID NO.: 13, and tenth passage SEQ ID NO: 14), and FIG. 3D, second GA, fifth passage (SEQ ID NOs: 16 and tenth passage SEQ ID NO: 17). However, SPBNGAK-GA-or SPBNGA-GAK-infected mice exhibited a significant loss of body weight and showed signs of neurological disease (Table 4) indicating that the Asn→Lys mutation is absent in both GA genes in order to preserve the non-pathogenic phenotype.

Genetic stability of SPBNGAS and SPBNGAS-GAS. To test their genetic stability, SPBNGAS and SPBNGAS-GAS were passaged i.c. five consecutive times in newborn mice. Nucleotide sequence analysis of RV RNA obtained from brain tissue of the 5th passage revealed no mutations or deletions in the GAS genes (SEQ ID NO: 5). The codon for $Ser_{194}$ remained unchanged after the 5th passage for the glycoprotein gene of SPBNGAS (SEQ ID NO: 19), for the first glycoprotein gene of SPBNGAS-GAS (SEQ ID NO: 21), and for the second glycoprotein gene of SPBNGAS-GAS (SEQ ID NO: 23) as shown in FIG. 8. Intracranial infection of adult immunocompetent mice with SPBNGAS and SPBNGAS-GAS obtained from the 5th mouse passage did not cause mortality, morbidity, or loss of body weight, indicating that non-pathogenic phenotype of these viruses is stable.

Figure 9:
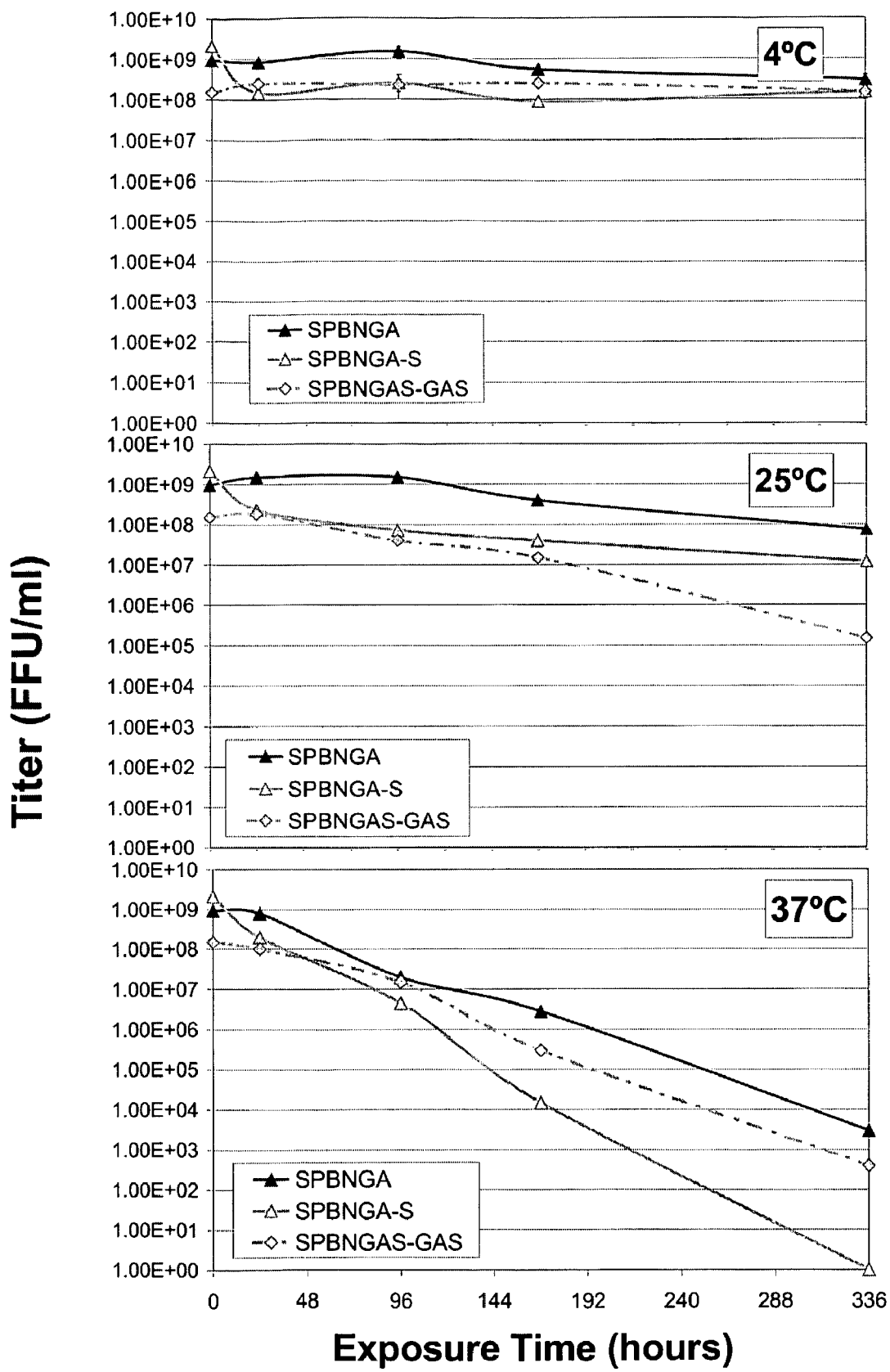
FIG. 9. Thermostability of recombinant RVs.

Thermostability of SPBNGAS and SPBNGAS-GAS. To exclude the possibility that the mutation of residue 194 the RV GA impairs the stability of the recombinant RVs, the viral titers of SPBNGA, SPBNGAS and SPBNGAS-GAS were determined after different times of exposure to different temperatures. As shown in FIG. 9, titers of all three viruses decreased only slightly after 7 days of exposure at 4° C. and 25° C. (~0.5 log). After exposure for 7 days at 37° C., titers of SPBNGA decreased by 2.5 logs and those of SPBNGAS and SPBNGAS-GAS decreased by 1 and 2.5 logs, respectively. These experiments indicate that the Asn→Ser mutation does not appear to decrease the thermostability of the virus. Sizable decreases in infectivity associated with the presence of extra genes were observed only at elevated temperatures (e.g., 37° C.).

TABLE 4

Mortality and morbidity of mice infected with recombinant RVs.

| Virus | Mortality Rate | Average loss of body weight (at day 8) | Average clinical score* (at day 8) |
|---|---|---|---|
| SPBNGA | 0/10 | 2.5% +/− 4.1 | 0 |
| SPBNGA-K | 1/10 | 13.8% +/− 4.4 | 1.0 +/− 0.4 |
| SPBNGA-S | 0/10 | 0.6% +/− 3.5 | 0 |
| SPBNGA-GA | 0/10 | −3.3% +/− 3.0 | 0 |
| SPBNGAK-GAK | 2/10 | 12.8% +/− 4.6 | 0.6 +/− 0.2 |
| SPBNGAS-GAS | 0/10 | 0.2% +/− 2.0 | 0 |
| SPBNGAK-GA | 0/10 | 9.7% +/− 3.9 | 0.6 +/− 3.0 |
| SPBNGA-GAK | 0/10 | 7.1% +/− 3.1 | 0.2 +/− 0.1 |

*Clinical Score: 0: healthy; 1: disordered movement; 2: ruffled fur, hunched back; 3: sever trembling, convulsions, 4: moribund, dehydration Although the present invention has been described in considerable detail with reference to certain preferred embodiments thereof, other versions are possible. Therefore the spirit and scope of the appended claims should not be limited to the description and the preferred versions contain within this specification.

REFERENCES

1. Martinez L. Global infectious disease surveillance. Int. J. Infect. Dis. 2000; 4(4):222-8.
2. Rupprecht C E, Smith J S, Fekadu M, Childs J E. The ascension of wildlife rabies: a cause for public health concern or intervention? Emerging Infect. Dis. 1995; 1(4): 107-14.
3. Meslin F-X, Fishbein D B, Matter H C. Rationale and prospects for rabies elimination in developing countries.

In: Rupprecht C E, Dietzschold B, Koprowski H, editors. Lyssaviruses. Berlin, Springer-Verlag, 1994: 1-26.

4. Aubert M F A, Masson E, Artois M, Barrat J. Oral wildlife rabies vaccination field trials in Europe with recent emphasis on France. In: Rupprecht C E, Dietzschold B, Koprowski H, editors. Lyssaviruses. Berlin, Springer-Verlag, 1994: 219-43.

5. Rupprecht C E, Blass L P, Krishnarao I, Smith K, Orciary L, Niezgoda M, Whitfield S, Hanlon C A. Human infection due to recombinant-rabies glycoprotein virus. N. Engl. J. Med. 2001; 345(8):582-6. Erratum in: N Engl J Med 2001; 345 (24):1784

6. Schnell M J, Mebatsion T, Conzelmann K-K. Infectious rabies viruses from cloned cDNA. EMBO J. 1994; 13(18): 4195-203.

7. Schnell M J, Foley H D, Siler C A, McGettigan J P, Dietzschold B, Pomerantz R J. Recombinant rabies virus as potential live-viral vaccines for HIV-1. Proc. Natl. Acad. Sci. USA 2000; 97(7): 3544-9.

8. Faber, M, Pulmanausahakul R, Hodawadekar S S., Spitsin S, McGettigan J P, Schnell M J, Dietzschold B. Overexpression of the rabies virus glycoprotein (G) results in enhancement of apoptosis and anti-viral immune response. J. Virol. 2002; 76(7): 3374-81.

9. Pulmanausahakul R, Faber M, Morimoto K, Spitsin S, Weihe E, Hooper D C, Schnell M J, Dietzschold B. Overexpression of cytochrome c by a recombinant rabies virus attenuates pathogenicity and enhances antiviral immunity. J. Virol. 2001; 75(22):10800-7.

10. Wiktor T J, MacFarlan R I, Foggin C M, Koprowski H. Antigenic analysis of rabies and Mokola virus from Zimbabwe using monoclonal antibodies. Dev. Biol. Stand. 1984; 57: 199-221.

11. Rupprecht C E, Charlton K M, Artois M, Casey G A, Webster W A, Campbell J B, Lawson K F, Schneider L G. Ineffectiveness and comparative pathogenicity of attenuated rabies virus vaccines for the striped skunk (Mephitis mephitis). J. Wildl. Dis. 1990; 26(1):99-102.

12. Vos A, Pommerening E, Neubert L, Kachel S, Neubert A. Safety studies of the oral rabies vaccine SAD B19 in striped skunk (Mephitis mephitis). J Wildl Dis. 2002; 38(2):428-31.

13. Hanlon C A, Niezgoda M, Morril P, Rupprecht C E. Oral efficacy of an attenuated rabies virus vaccine in skunks and raccoons. J Wildl Dis. 2002; 38(2):420-7.

14. Blancou J, Meslin F-X. Modified live-virus rabies vaccines for oral immunization of carnivores. In: Meslin F-X, Kaplan M M, Koprowski H. editors. Laboratory techniques in rabies. World Health Organization, Geneva. Fourth edition, 1996: 324-37.

15. WHO. Report of WHO/APHIS consultation on baits and baiting delivery systems for oral immunization of wildlife against rabies. 1990 July 10-12; Denver, Colo. WHO/Rab Res/90.36.

16. Mebatsion T. Extensive attenuation of rabies virus by simultaneously modifying the dynein light chain binding site in the P protein and replacing Arg333 in the G protein. J. Virol. 2001; 75(23): 11496-502.

17. Rupprecht C E, Hanlon C A, Blanton J, Managan J, Morril P, Murphy S, Niezgoda M, Orciari L, Dietzschold B. Efficacy of experimental oral vaccination of dogs using recombinant rabies viruses. XII International Meeting on Advances in Rabies Research and Control in the Americas, Philadelphia, Pa., Oct. 19-24, 2003.

TABLE 5

Mortality and morbidity of mice infected with recombinant RVs.

| Virus | Mortality Rate | Average loss of body weight (at day 8) | Average clinical score* (at day 8) |
|---|---|---|---|
| SPBNGA | 0/10 | 2.5% +/− 4.1 | 0 |
| SPBNGA-K | 1/10 | 13.8% +/− 4.4 | 1.0 +/− 0.4 |
| SPBNGA-S | 0/10 | 0.6% +/− 3.5 | 0 |
| SPBNGA-GA | 0/10 | −3.3% +/− 3.0 | 0 |
| SPBNGAK-GAK | 2/10 | 12.8% +/− 4.6 | 0.6 +/− 0.2 |
| SPBNGAS-GAS | 0/10 | 0.2% +/− 2.0 | 0 |
| SPBNGAK-GA | 0/10 | 9.7% +/− 3.9 | 0.6 +/− 3.0 |
| SPBNGA-GAK | 0/10 | 7.1% +/− 3.1 | 0.2 +/− 0.1 |

*Clinical Score: 0: healthy; 1: disordered movement; 2: ruffled fur, hunched back; 3: sever trembling, convulsions; 4: moribund, dehydration

What is claimed is:

1. A non-pathogenic recombinant rabies virus comprising a mutated G gene that encodes a rabies virus glycoprotein wherein the amino acid 194 is serine and the amino acid 333 is glutamic acid in the glycoprotein.

2. A non-pathogenic recombinant rabies virus according to claim 1 which expresses a foreign protein antigen.

3. A non-pathogenic recombinant rabies virus according to claim 2, wherein the expressed foreign protein antigen is an antigen of a pathogen.

4. A non-pathogenic recombinant rabies virus according to claim 1, which expresses a pro-apoptotic protein.

5. A non-pathogenic recombinant rabies virus according to claim 4, which expresses as a pro-apoptotic protein at least one additional mutated G gene that encodes a rabies virus glycoprotein wherein amino acid 194 is serine and amino acid 333 is glutamic acid in the glycoprotein.

6. A non-pathogenic recombinant rabies virus according to claim 4, which expresses cytochrome c as a pro-apoptotic protein.

7. A composition comprising a non-pathogenic recombinant rabies virus according to claim 1, and a pharmaceutically acceptable carrier.

8. A method of protecting an animal susceptible to being infected with rabies virus comprising inoculating the animal with an effective amount of the non-pathogenic recombinant rabies virus according to claim 1.

9. A recombinant rabies virus expressing a glycoprotein comprising at least one glycoprotein gene sequence of SEQ ID NO 5.

10. A modified glycoprotein gene comprising SEQ ID NO 5.

* * * * *